United States Patent [19]

Milberger et al.

[11] 4,292,203

[45] Sep. 29, 1981

[54] OXIDATION CATALYSTS

[75] Inventors: Ernest C. Milberger, Solon; Eunice K. T. Wong, Cleveland, both of Ohio

[73] Assignee: The Standard Oil Company, Cleveland, Ohio

[21] Appl. No.: 130,958

[22] Filed: Mar. 17, 1980

Related U.S. Application Data

[60] Division of Ser. No. 784,003, Apr. 4, 1977, Pat. No. 4,155,920, and a continuation-in-part of Ser. No. 901,888, May 1, 1978, Pat. No. 4,240,931.

[51] Int. Cl.³ .................... B01J 27/24; B01J 29/06; B01J 23/10; B01J 23/14
[52] U.S. Cl. .................... 252/438; 252/455 R; 252/456; 252/462; 252/464; 252/468; 252/469; 252/470
[58] Field of Search .................... 252/438, 455 R, 456, 252/462, 464, 468, 469, 470

[56] References Cited

U.S. PATENT DOCUMENTS

| | | | |
|---|---|---|---|
| 3,341,471 | 9/1967 | Callahan et al. | 252/469 X |
| 3,387,038 | 6/1968 | Koch | 252/468 X |
| 3,595,911 | 7/1971 | Ball | 252/469 X |
| 3,907,834 | 9/1975 | Milberger et al. | 252/470 X |
| 3,956,378 | 5/1976 | Grasselli et al. | 562/547 X |
| 3,984,353 | 10/1976 | Sergunkin et al. | 252/462 X |
| 3,994,833 | 11/1976 | Jouy et al. | 252/469 |
| 4,021,427 | 5/1977 | Dolhyj et al. | 260/346.75 |
| 4,052,417 | 10/1977 | Slinkard et al. | 260/346.75 |
| 4,065,468 | 12/1977 | Grasselli et al. | 260/346.75 |
| 4,129,592 | 12/1978 | Slinkard et al. | 252/456 X |

FOREIGN PATENT DOCUMENTS

| | | |
|---|---|---|
| 1900111 | 8/1970 | Fed. Rep. of Germany . |
| 1157117 | 7/1969 | United Kingdom . |
| 1377325 | 12/1974 | United Kingdom . |

OTHER PUBLICATIONS

Kirk–Othmer Encyclopedia of Chemical Technology, 2nd Completely Revised Edition, vol. 13, pp. 654–655.

*Primary Examiner*—Delbert E. Gantz
*Assistant Examiner*—William G. Wright
*Attorney, Agent, or Firm*—Larry W. Evans; Joseph G. Curatolo; Herbert D. Knudsen

[57] ABSTRACT

Maleic anhydride is produced by the oxidation of 1,3-butadiene, n-butylenes, crotonaldehyde and furan with molecular oxygen in the vapor phase in the presence of catalytic oxides of antimony, molybdenum, at least one element selected from the group consisting of niobium, zirconium, titanium and tantalum and optionally a reducing agent capable of reducing at least part of the molybdenum in the catalyst to a valence state below +6 selected from the group consisting of hydrazine hydrate, molybdenum, tungsten, magnesium, aluminum, and nickel. This catalyst may optionally contain one or more elements selected from the group consisting of Li, Ag, Ce, Cd, Co, As, Si, Zn, Ge, Bi, Ru, Pt, U, Al and Ni. Preferred catalysts contain Nb, Zr, Ta or Ti in combination with Nb, Zr, or Ta. Especially desirable yields of maleic anhydride are obtained from 1,3-butadiene in the presence of a catalyst wherein molybdenum metal is used as a reducing agent.

12 Claims, No Drawings

OXIDATION CATALYSTS

REFERENCE TO RELATED APPLICATIONS

This application is a continuation in part of application Ser. No. 901,888 filed May 1, 1978 now U.S. Pat. No. 4,240,931; and this application is also a division of application U.S. Ser. No. 784,003 filed Apr. 4, 1977 now U.S. Pat. No. 4,155,920.

BACKGROUND OF THE INVENTION

Generally, in the commercial production of maleic anhydride by the catalytic oxidation of hydrocarbons, it is of ultimate importance to use catalysts which give high conversions of hydrocarbons to maleic anhydride.

Maleica anhydride is conventionally prepared by the oxidation of benzene; however, high percentages of converted benzene are lost in the form of carbon oxides. This process creates unnecessary waste in that two carbon atoms are oxidized to useless waste.

The oxidation of 1,3-butadiene to produce maleic anhydride eliminates this waste. This process has been conducted before in the art using various catalysts, for example West German Patent No. 1099111 discloses the preparation of maleic anhydride by the catalytic vapor phase oxidation of 4-carbon hydrocarbons in the presence of catalysts of the composition $AO_3$-$B_2O_5$-$M_2O_5$-$N_xO$-$R_2O$ (in which A is Cr, Mo, W or U; B is V or Nb; M is P, As, Sb or Bi; N is Cu, Ag, Fe, Co or Ni; R is Li, Na, K, Cs or Rb; x is 1–2). U.S. Pat. No. 3,907,834 discloses the preparation of maleic anhydride from n-butylenes, 1,3-butadiene, crotonaldehyde and furan in the presence of a catalyst containing antimony, molybdenum, and a reducing agent selected from the group consisting of molybdenum, tungsten, magnesium, aluminum and nickel. British Pat. No. 1,157,117 discloses the production of maleic anhydride from a saturated aliphatic hydrocarbon having 4 carbon atoms in the molecule or an unsaturated aliphatic hydrocarbon having 4 or 5 atoms in the molecule in the presence of a catalyst comprising an oxide of molybdenum and at least one other oxide of tin, antimony, titanium, iron or tungsten.

U.S. Pat. No. 4,907,834 to Milberger, et al. discloses the oxidation of four-carbon hydrocarbons to maleic anhydride in the presence of catalysts containing molybdenum, antimony and at least one element selected from the group consisting of molybdenum, tungsten, magnesium, aluminum and nickel. Patentees state at column 3, lines 1 to 5 that said catalyst may be supported on a carrier material such as silica, zirconia, calcium stabilized zirconia, titania, alumina, thoria, silicon carbide, clay, diatomaceous earth and the like. Example 8 shows the preparation of a catalyst of the formula 80% ($Sb_4Mo_6O_{24}$)-20% $TiO_2$. The support material, $TiO_2$, disclosed in this patent is added as a chemically inactive ingredient.

U.S. Pat. No. 4,065,468 to Grasselli, et al. discloses the preparation of maleic anhydride from n-butane in the presence of a catalyst containing antimony, molybdenum, at least one member selected from the group consisting of iron and vanadium, and optionally one or more oxidesa of aluminum, boron, tellurium, chromium, cobalt, nickel, copper, bismuth, phosphorus, titanium, and tungsten. Specifically exemplified at columns 5 and 6 in Example 7 is use of a catalyst of the formula 80% by weight of $TiFeSb_3Mo_6O_{29}$ and 20% by weight $SiO_2$, wherein the source of titanium component is titanium dioxide.

U.S. Pat. No. 4,052,417 to Slinkard, et al. discloses the preparation of maleic anhydride from butane in the presence of a catalyst comprising a reduced calcined coprecipitate of a molybdenum compound and a phosphorus compound, and optionally the catalyst contains one or more catalyst metal elements selected from titanium, vanadium, niobium and bismuth.

U.S. Pat. No. 4,021,427 to Dolhyj, et al, discloses the preparation of maleic anhydride from 1,3-butadiene, n-butylene, crotonaldehyde and furan in the presence of a catalyst containing antimony, molybdenum, vanadium and lithium, cerium or mixtures thereof, wherein one element selected from the group consisting of calcium, iron, tungsten, magnesium, aluminum and nickel is optionally added as a reducing agent.

U.S. Pat. No. 3,956,378 to Grasselli, et al. discloses the catalytic oxidation of olefins to unsaturated aldehydes and acids and the ammoxidation of olefins to unsaturated nitriles using a catalyst containing molybdenum, antimony, oxygen, at least one element selected from the group consisting of Te, W, Ti, Mn, Ni, Fe, Cu, Pb, Re, Bi, Sn, U, Cr, P and B, and optionally a member selected from the group consisting of Mo, W, Al, Ni, and S.

The primary object of the present invention is to provide a process for producing maleic anhydride using novel catalysts with improved yields of maleic anhydride and decreased waste byproducts.

It is a further object of this invention to provide a method for making the novel and improved catalyst of the character indicated.

SUMMARY OF THE INVENTION

In accordance with the present invention has been discovered a process for the preparation of maleic anhydride comprising contacting a mixture of an unsaturated organic compound selected from the group consisting of n-butylenes, 1,e-butadiene, crotonaldehyde and furan and an oxygen-containing gas with a catalyst at a temperature in the range of from about 250° C. to 600° C., under a pressure of from about 1 to 500 psi, and wherein the molar ratio of oxygen to the organic compound is in the ragne of from 2:1 to 40:1, the improvement comprising:

using as the catalyst a catalyst of the formula

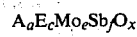

$$A_aE_cMo_eSb_fO_x$$

wherein
A is at least one element selected from the group consisting of niobium, zirconium, titanium and tantalum;
E is a member selected from the group consisting of hydrazine hydrate, a finely divided metal of molybdenum, tungsten, magnesium, aluminum, or nickel;
and wherein
a is a number from 0.01 to 6;
c is a number from 0 to 0.2;
e and f are numbers from 1 to 9;
x is a number which satisfies the valence requirements of the other elements present;
and wherein at least some of the molybdenum in the catalyst is maintained at a valence state below +6;
said catalyst optionally containing one or more elements selected from the group consisting of lithium, silver, cerium, cadmium, cobalt, arsenic, silicon, zinc, germanium, bismuth, ruthenium, platinum and uranium.

Maximum results are achieved when the starting material is 1,3-butadiene. Improved results are obtained when the basic antimony-molybdenum catalyst is promoted with single elements of tantalum, zirconium, titanium or niobium but, from the standpoint of optimum benefits and catalyst effectiveness, it is preferred that a combination of titanium and niobium or titanium and zirconium be incorporated in the catalyst to enhance the activity of the basic catalyst system.

As noted, the catalyst employed in the present invention may be any catalyst delineated by the above formula, however, preferred catalysts are represented by the formula $$A_aD_bE_cTi_dMo_eSb_fO_x$$

wherein
- A is at least one element selected from the group consisting of niobium, zirconium, and tantalum;
- D is at least one element selected from the group consisting of cadmium, cobalt, arsenic, nickel, lithium and cerium;
- E is a member selected from the group consisting of hydrazine hydrate, a finely divided metal of molybdenum, tungsten, magnesium, aluminum or nickel;

wherein
- a and d are numbers from 0 to 3;
- b is a number from 0 to 1;
- c is a number from 0 to 0.2;
- a+d is not zero;
- e and f are numbers from 1 to 9;
- x is a number which satisfies the valence requirements of the other elements present;

and wherein at least some of the molybdenum in the catalyst is maintained at a valence state below +6.

Excellent results are achieved using catalysts wherein D is at least one element selected from the group consisting of arsenic, lithium and cerium. Catalysts of particular interest are described wherein a and/or d are numbers from 0.01 to 3 or wherein b is 0 to 0.5. Especially desirable results are observed using catalysts wherein a and d are numbers from 0.01 to 1.0 and b is zero.

Also preferred in the invention are those catalysts wherein E is added to the catalyst as molybdenum metal. After the catalyst is prepared, this metal may be at least partially present in the form of an oxide or oxide complex. The catalysts which are prepared using molybdenum metal are preferably those wherein c is 0.001 to 0.2 and e and f are numbers from 1.0 to 8.0.

Especially preferred catalysts compositions are described by the formulae:

$$A_aE_cMo_eSb_fO_x$$

wherein
- A is at least one element selected from the group consisting of niobium, tantalum and zirconium;
- E is a member selected from the group consisting of hydrazine hydrate, a finely divided metal of molybdenum, tungsten, magnesium, aluminum or nickel;

and wherein
- a is a number from 0.01 to 6;
- c is a number from 0 to 0.2;
- e and f are numbers from 1 to 9;
- x is a number which satisfies the valence requirements of the other elements present;

and wherein at least some of the molybdenum in the catalyst is maintained at a valence state below +6.

said catalyst optionally containing one or more elements selected from the group consisting of lithium, silver, cerium, cadmium, cobalt, arsenic, silicon, zinc, germanium, bismuth, ruthenium, platinum and uranium; or a catalyst composition of the formula $$A_aE_cMo_eSb_fO_x$$

wherein
- A is titanium in combination with at least one element selected from the group consisting of zirconium, niobium and tantalum;
- E is a member selected from the group consisting of hydrazine hydrate, a finely divided metal of molybdenum, tungsten, magnesium, aluminum or nickel;

and wherein
- a is a number from 0.01 to 6;
- c is a number from 0 to 0.2;
- e and f are numbers from 1 to 9;
- x is a number which satisfies the valence requirements of the other elements present;

and wherein at least ome of the molybdenum in the catalyst is maintained at a valence state below +6;

said catalyst optionally containing one or more elements selected from the group consisting of lithium, silver, cerium, cadmium, cobalt, arsenic, silicon, zinc, germanium, bismuth, ruthenium, platinum, and uranium; or a catalyst composition of the formula $$A_aD_bE_cTi_dMo_eSb_fO_x$$

wherein
- A is at least one element selected from the group consisting of niobium, zirconium and tantalum;
- D is at least one element selected from the group consisting of cadmium, cobalt, arsenic, lithium and cerium;
- E is a member selected from the group consisting of hydrazine hydrate, a finely divided metal of molybdenum, tungsten, magnesium or aluminum;

wherein
- a and d are numbers from 0 to 3;
- b is a number from 0.01 to 1;
- c is a number from 0 to 0.2;
- a+d is not zero;
- e and f are numbers from 1 to 9;
- x is a number which satisfies the valence requirements of the other elements present;

and wherein
at least some of the molybdenum in the catalyst is maintained at a valence state below +6; or a catalyst composition of the formula $$A_aD_bE_cTi_dMo_eSb_fO_x$$

wherein
- A is at least one element selected from the group consisting of niobium, zirconium and tantalum;
- D is at least one element selected from the group consisting of cadmium, cobalt, arsenic, nickel, lithium and cerium;

E is a member selected from the group consisting of hydrazine hydrate, a finely divided metal of molybdenum, tungsten, magnesium, aluminum or nickel;
wherein
a is 0.01 to 3;
b is a number from 0 to 1;
c is a number number from 0 to 0.2;
d is 0 to 3;
e and f are numbers from 1 to 9;
x is the number which satisfies the valence requirements of the other elements present;
and wherein at least some of the molybdenum in the catalyst is maintained at a valence state below +6; or a catalyst composition of the formula $$A_a E_c Ti_d Mo_e Sb_f O_x$$

wherein
A is at least one element selected from the group consisting of niobium, zirconia, and tantalum;
E is at least one element selected from the group consisting of hydrazine hydrate, a finely divided metal of molybdenum, tungsten, magnesium, aluminum or nickel;
wherein
a and d are numbers from 0.01 to 3;
c is a number from 0 to 0.2;
e and f are numbers from 1 to 9;
x is a number which satisfies the valence requirements of the other elements present;
and wherein at least some of the molybdenum in the catalyst is maintained at a valence state below +6.

Excellent results are achieved using catalysts wherein D is at least one element selected from the group consisting of arsenic, lithium and cerium. Catalysts of particular interest are described wherein a and d are numbers from 0.01 to 3 or wherein b is 0 to 0.5. Especially desirable results are observed using catalysts wherein a and d are numbers from 0.01 to 1.0 and b is zero.

Also preferred in the invention are those catalysts wherein E is added to the catalyst as molybdenum metal. After the catalyst is prepared, this metal may be at least partially present in the form of an oxide or oxide complex. The catalysts which are prepared using molybdenum metal are preferably those wherein c is 0.001 to 0.2 and e and f are numbers from 1.0 to 8.0.

The method used for preparing the catalyst of this invention is critical to the process for producing maleic anhydride. The method employed departs from the classical procedures involving coprecipitation or impregnation techniques and preferably involves contacting the compound containing hexavalent molybdenum with a controlled amount of a reducing agent. By the preferred procedure of the invention a compound containing hexavalent molybdenum, preferably molybdenum trioxide, ammonium heptamolybdate or mixture thereof, in an aqueous suspension is prereduced in a controlled manner so that at least some of the molybdenum is reduced to a valence state below +6 before the compound containing hexavalent molybdenum is mixed with the antimony trioxide. For example, a mixture of molybdenum trioxide and ammonium heptamolybdate may be contacted with a given amount of molybdenum metal powder to effect a certain and reproducible degree of reduction. A wide range of reducing agents can be employed to effect the desired reduction. Representative examples of strong reducing agents include finely divided or colloidal metals of molybdenum, tungsten, magnesium, aluminum or nickel and hydrazine hydrate.

Representative examples of weak reducing agents are lower valent antimony oxides and salts and other metal oxides or salts containing metals in their lower oxidation states. When powdered metals are employed, the amount of metal reacted ranges from 0.01 to 0.2 atom per mole of the hexavalent molybdenum present.

One method of preparing the catalyst involves refluxing an aqueous slurry of antimony trioxide, molybdenum trioxide and/or ammonium heptamolybdate and compounds containing the respective promoter elements for a period of one-half hour to 16 hours. The amount of water present in solution can range from 500 to 2000 mls. per mole of the molybdenum present. During this period the slurry darkens. Water is removed from the slurry by evaporation until a thick homogeneous material is obtained which on drying at 110°–130° C. overnight emerges as a dark blue-green or blue-gray solid. It is hypothesized that the darker color which develops in the catalyst is the result of the reduction of molybdenum, at least in part, to a lower oxidation state in the oxidation reduction reaction occurring between hexavalent molybdenum and trivalent antimony.

Although preferably the compound containing hexavalent molybdenum is prereduced before reaction with antimony trioxide, beneficial results are achieved by reacting the compound containing hexavalent molybdenum with antimony trioxide followed by reaction with the reducing agent, or by reacting the three components together followed by the addition of compounds containing the respective promoter elements.

The catalyst may be activated by calcining it in air at a temperature of about 350° C. to 700° C. for a period of up to five hours or more. By the preferred procedure of the invention, the catalyst is not calcined prior to being reacted with the desired hydrocarbon. The hydrocarbon reacted may be n-butylenes, 1,3-butadiene, crotonaldehyde, furan or a mixture thereof. Preferred is the use of 1,3-butadiene or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C. to about 600° C. are employed with temperatures of 325° C. to 480° C. being preferred.

The catalyst may be used alone or a support could be employed. Suitable supports include silica, alumina, clay, Alundum, silicon carbide, boron phosphate, zirconia, titania, thoria, diatomaceous earth, and aluminum phosphate. The catalysts are conveniently used in a fixed-bed reactor using tablets, pellets or the like or in a fluid-bed reactor using a catalyst preferably having a particle size of less than about 300 microns. The contact time may be as low as a fraction of a second or as high as 50 seconds. The reaction may be conducted at atmospheric, superatmospheric or subatmospheric pressure.

Excellent results are obtained using a coated catalyst consisting essentially of an inert support material having a diameter of at least 20 microns and an outer surface and a continuous coating of said active catalyst on said inert support strongly adhering to the outer surface of said support.

By use of these coated catalysts in the reaction to produce maleic anhydride, a very low exotherm is realized allowing for better control of the reaction. High single pass yields are exhibited and the elimination of undesirable byproducts is obtained.

The special coated catalyst consists of an inner support material having an outside surface and a coating of the active catalytic material on this outside surface. These catalysts can be prepared by a number of different methods.

The support material for the catalyst forms the inner core of the catalyst. This is an essentially inert support and may have substantially any particle size, although a diameter of greater than 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Especially preferred among these supports are Alundum, silica, alumina and alumina-silica.

The catalysts may contain essentially any proportions of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is to partially wet the support material with a liquid. The support should not be wet on the oustide surface of the total mass. It should appear to be dry to the touch. If the support is wet, then the active catalytic material may agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum or jar and adding the active catalytic material. This is very economically done.

Using the catalysts of the invention in the preparation of maleic anhydride, excellent yields are obtained in a convenient reaction with low amounts of byproducts.

SPECIFIC EMBODIMENTS

Comparative Examples A to F and Examples 1 to 43

Preparation of Maleic Anhydride Using Catalysts Containing Promoters of Invention Compared with Use of Base Catalyst A 20 cc. fixed-bed reactor was constructed of a 1.3 cm. inside diameter stainless steel tubing equipped with a full length 0.3 cm. axial thermowell. Catalysts prepared as described below were charged to the reactor and heated to the reaction temperature and 1,3-butadiene was reacted with air in the proportions specified in TABLES I to V at an apparent contact time of 3 to 4 seconds. The total usable acids were recovered and analyzed. Maleic anhydride was determined by potentiometric titration.

Comparative Example A and Examples 1 to 10

The catalysts were prepared as follows:

Comparative Example A $SbMo_3O_x + Mo°_{0.06}$

A slurry was prepared consisting of 72.0 grams of molybdenum trioxide (Baker green), 0.96 grams of molybdenum metal powder (Sylvania) and 1000 mls. of distilled water. This aqueous slurry was refluxed for two hours followed by the addition of 24.27 grams of antimony trioxide; the resulting mixture was refluxed an additional hour, evaporated to a thick paste, dried overnight at 110° C. to 130° C. and ground and screened to 20-30 mesh.

Examples 1 to 39—Reaction of 1,3-Butadiene Using Various Catalysts of the Invention

Examples 1 to 10

Catalysts of the invention were employed to prepare maleic anhydride from 1,3-butadiene in the same manner shown in Comparative Example A. The catalysts for these experiments were prepared as follows:

Example 1

$SbMo_3Ti_{0.6}O_x + Mo°_{0.06}$

A slurry was prepared consisting of 72.0 grams of molybdenum trioxide, 0.96 grams of molybdenum metal powder, 7.98 grams of pigment grade titanium dioxide (Dupont) and 1000 mls. of distilled water. This aqueous slurry was refluxed for two hours followed by the addition of 24.27 grams of antimony trioxide; the resulting mixture was refluxed an additional hour, evaporated to a thick paste, dried overnight at 110°-130° C., and ground and screened to 20-30 mesh.

Examples 2 and 3

Catalysts of the formulae $SbMo_3Ti_{0.3}O_x + Mo°_{0.06}$ and $SbMo_3Ti_{1.2}O_x + Mo°_{0.06}$ were prepared in the same manner described in Example 1 using 3.99 grams of anatase titanium dioxide or 15.96 grams of anatase titanium dioxide, respectively.

Examples 4 to 6

In the same manner described in Example 1, catalysts of the formulae $SbMo_3Nb_{0.6}O_x + Mo°_{0.06}$, $SbMo_3Ta_{0.6}O_x + Mo°_{0.06}$ and $SbMo_3Zr_{0.6}O_x + Mo°_{0.06}$ were prepared by replacing the titanium dioxide with 13.32 grams of niobium pentoxide, 22.2 grams of tantalum pentoxide, or 12.3 grams of zirconium dioxide, respectively.

Example 7

Part A. $SbMo_3Ti_{0.6}Nb_{0.1}O_x + Mo°_{0.06}$

A slurry was prepared consisting of 72.0 grams of molybdenum trioxide, 0.96 grams of molybdenum metal powder, 7.98 grams of high surface area titanium dioxide, 2.22 grams of niobium pentoxide and 1000 mls. of distilled water. This aqueous slurry was refluxed for two hours followed by the addition of 24.27 grams of antimony trioxide; the resulting mixture was refluxed an additional hour, evaporated to a thick paste, dried over the weekend at 110° C., and ground and screened to 20-30 mesh size.

Part B. 33%(SbMo$_3$Ti$_{0.6}$Nb$_{0.1}$O$_x$+Mo°$_{0.06}$)+66 2/3% Alundum

A catalyst was prepared in the same manner described in Part A, except the dry catalytic particles were ground and screened to less than 50 mesh size and coated on 10–30 mesh SA 5209 Alundum balls by taking 40 grams of Alundum, partially wetting the Alundum with 3.6 grams of water and adding 20 grams of active catalyst prepared above in 5 equal portions. During and after each addition, the Alundum was rolled in a glass gar. The powder was evenly coated onto the surface of the Alundum and the final product was dried. A hard uniform coated catalyst was obtained that consisted of the Alundum support with the continuous, strongly adhering coating of the active catalyst. The catalyst was then dried in an oven at 110°–130° C. for 16 hours.

Examples 8 to 10

In the same manner described in Example 7, Part A catalysts of the formulae SbMo$_3$Ti$_{0.6}$Zr$_{0.1}$O$_x$+Mo°$_{0.06}$, SbMo$_3$Ti$_{0.6}$As$_{0.1}$O$_x$+Mo°$_{0.06}$, and SbMo$_3$Ti$_{0.6}$Ce$_{0.1}$O$_x$+Mo°$_{0.06}$ were prepared by replacing the niobium pentoxide with 2.05 grams of zirconium dioxide (Zr Corp. of America) 1.65 grams of arsenous trioxide, or 2.87 grams of cerium dioxide, respectively.

Comparative Examples B and C and Examples 11 to 37

The results of the experiments in the oxidation of 1,3-butadiene to produce maleic anhydride are shown in TABLES I to IV below. The results are stated in terms of per pass conversion which is defined as $$\frac{\text{Grams of carbon as maleic anhydride obtained}}{\text{Grams of carbon as organic starting material}} \times 100$$

In the same manner described above, catalysts of the invention may be effectively utilized in the oxidation of furan, n-butylenes and crotonaldehyde.

TABLE I

Performance of Catalysts of the Invention Compared with Base Sb—Mo Catalyst in the Preparation of Maleic Anhydride

| Example | Catalyst | Temp °C. Bath | Temp °C. Bed | Molar Feed Ratio Air/BD | Per Pass Conversion, % Total Acid | Per Pass Conversion, % MAA |
|---|---|---|---|---|---|---|
| Comp. B | SbMo$_3$O$_x$ + Mo°$_{0.06}$ | 369 | 383 | 25.12 | 68.79 | 63.93 |
| Comp. C | SbMo$_3$O$_x$ + Mo°$_{0.06}$ | 387 | 407 | 25.51 | 66.82 | 61.13 |
| 11 | SbMo$_3$Ti$_{0.3}$O$_x$ + Mo°$_{0.06}$ | 371 | 389 | 27.28 | 73.61 | 70.91 |
| 12 | SbMo$_3$Ti$_{0.6}$O$_x$ + Mo°$_{0.06}$ | 371 | 381 | 26.39 | 73.45 | 70.09 |
| 13 | SbMo$_3$Ti$_{0.6}$O$_x$ + Mo°$_{0.06}$ | 399 | 413 | 26.55 | 75.10 | 71.45 |
| 14 | SbMo$_3$Ti$_{1.2}$O$_x$ + Mo°$_{0.06}$ | 372 | 385 | 27.02 | 74.34 | 71.07 |
| 15 | SbMo$_3$Nb$_{0.6}$O$_x$ + Mo°$_{0.06}$ | 371 | 390 | 27.69 | 74.86 | 71.74 |
| 16 | SbMo$_3$Ta$_{0.6}$O$_x$ + Mo°$_{0.06}$ | 373 | 389 | 27.09 | 78.70 | 74.70 |
| 17 | SbMo$_3$Zr$_{0.6}$O$_x$ + Mo°$_{0.06}$ | 372 | 385 | 29.49 | 76.64 | 72.61 |

TABLE II

Preparation of Maleic Anhydride from 1,3-Butadiene Using the Catalyst SbMo$_3$Ti$_{0.6}$Zr$_{0.1}$O$_x$ + Mo°$_{0.06}$

| Example | Temp °C. Bath | Temp °C. Bed | Molar Feed Ratio Air/BD | Per Pass Conversion, % Total Acid | Per Pass Conversion, % MAA | Hours on Stream |
|---|---|---|---|---|---|---|
| 18 | 396 | 404 | 29.60 | 75.50 | 72.25 | 17.5 |
| 19 | 406 | 417 | 30.22 | 75.07 | 72.29 | 18.1 |
| 20 | 396 | 404 | 32.71 | 80.82 | 78.06 | 134.2 |
| 21 | 387 | 401 | 31.80 | 81.08 | 77.98 | 136.8 |
| 22 | 381 | 391 | 32.26 | 76.43 | 74.49 | 138.5 |

TABLE III

Preparation of Maleic Anhydride from 1,3-Butadiene Using the Catalyst SbMo$_3$Ti$_{0.6}$Nb$_{0.1}$O$_x$ + Mo°$_{0.06}$

| Example | Temp °C. Bath | Temp °C. Bed | Molar Feed Ratio Air/BD | Per Pass Conversion, % Total Acid | Per Pass Conversion, % MAA | Hours on Stream |
|---|---|---|---|---|---|---|
| 23 | 385 | 396 | 31.34 | 76.48 | 73.21 | 17.8 |
| 24 | 386 | 395 | 27.71 | 75.23 | 72.36 | 20.3 |
| 25 | 392 | 404 | 30.21 | 76.69 | 73.48 | 22.0 |
| 26 | 392 | 403 | 32.05 | 81.52 | 78.0 | 38.5 |
| 27 | 400 | 416 | 31.19 | 78.0 | 75.73 | 40.8 |
| 28 | 392 | 409 | 30.40 | 78.18 | 75.93 | 43.8 |
| 29 | 388 | 400 | 31.58 | 80.57 | 77.85 | 60 |
| 30* | 387 | 394 | 84.72 | 80.81 | 78.61 | 63.7 |
| 31 | 387 | 406 | 22.12 | 74.61 | 70.57 | 65.4 |
| 32 | 384 | 399 | 33.03 | 80.08 | 75.67 | 131.5 |

*1.24 seconds contact time

TABLE IV

Preparation of Maleic Anhydride from 1,3-Butadiene Various Catalysts of the Invention

| Example | Catalyst | Temp °C. Bath | Temp °C. Bed | Molar Feed Ratio Air/BD | Per Pass Conversion, % Total Acid | Per Pass Conversion, % MAA |
|---|---|---|---|---|---|---|
| 33 | SbMo$_3$Ti$_{0.6}$Nb$_{0.1}$O$_x$ + Mo°$_{0.06}$ (coated) | 402 | 406 | 37.22 | 79.41 | 76.38 |
| 34 | SbMo$_3$Ti$_{0.6}$Nb$_{0.1}$O$_x$ + Mo°$_{0.06}$ (coated) | 412 | 416 | 36.88 | 77.73 | 75.11 |
| 35 | SbMo$_3$Ti$_{0.6}$As$_{0.1}$O$_x$ + Mo°$_{0.06}$ | 412 | 426 | 28.61 | 78.37 | 74.90 |
| 36 | SbMo$_3$Ti$_{0.6}$As$_{0.1}$O$_x$ + Mo°$_{0.06}$ | 410 | 419 | 72.48 | 75.37 | 72.58 |
| 37 | SbMo$_3$Ti$_{0.6}$Ce$_{0.1}$O$_x$ + Mo°$_{0.06}$ | 385 | 404 | 28.2 | 75.33 | 73.17 |

Examples 38 to 43

The catalysts SbMo$_3$Ti$_{0.6}$Nb$_{0.1}$O$_x$+Mo°$_{0.06}$ and SbMo$_3$Ti$_{0.6}$Zr$_{0.1}$O$_x$+Mo°$_{0.06}$ were prepared using a mixture of molybdenum trioxide and ammonium heptamolybdate. The experimental results showing the oxidation of 1,3-butadiene in the presence of these catalysts appear in TABLE V.

These catalysts were prepared as follows:

Example 38

$SbMo_3Ti_{0.6}Nb_{0.1}O_x + Mo°_{0.06}$

A slurry was prepared consisting of 54.0 grams of molybdenum trioxide, 22.07 grams of ammonium heptamolybdate, 0.96 grams of molybdenum metal powder, 7.98 grams of pigment grade titanium dioxide, 2.22 grams of niobium pentoxide and 1000 mls. of distilled water. This aqueous slurry was refluxed for two hours followed by the addition of 24.27 grams of antimony trioxide; the resulting mixture was refluxed an additional hour, evaporated to a thick paste, dried over the weekend at 110° C., and ground and screened to 20–30 mesh size.

Example 39

In the same manner described in Example 38, a catalyst of the formula $SbMo_3Ti_{0.6}Zr_{0.1}O_x + Mo°_{0.06}$ was prepared by replacing the niobium pentoxide with 2.05 grams of zirconium dioxide.

TABLE V

Effect of Using a Mixture of Molybdenum Trioxide And Ammonium Heptamolybdate in the Preparation of Catalysts of the Invention

| Example | Catalyst | Temp °C. Bath | Temp °C. Bed | Molar Feed Ratio Air/BD | Per Pass Conversion, % Total Acid | Per Pass Conversion, % MAA | Hours on Stream |
|---|---|---|---|---|---|---|---|
| 40 | $SbMo_3Ti_{0.6}Nb_{0.1}O_x + Mo°_{0.06}$ | 360 | 371 | 30.04 | 78.86 | 74.67 | 23 |
| 41 | $SbMo_3Ti_{0.6}Nb_{0.1}O_x + Mo°_{0.06}$ | 372 | 382 | 30.53 | 82.12 | 77.98 | 21.6 |
| 42 | $SbMo_3Ti_{0.6}Zr_{0.1}O_x + Mo°_{0.06}$ | 371 | 388 | 34.8 | 80.23 | 76.3 | 286 |
| 43 | $SbMo_3Ti_{0.6}Zr_{0.1}O_x + Mo°_{0.06}$ | 385 | 403 | 35.4 | 83.35 | 78.7 | 407.8 |

We claim:
1. A catalyst composition of the formula

$$A_aE_cMo_eSb_fO_x$$

wherein
A is at least one element selected from the group consisting of tantalum and zirconium;
E is a member selected from the group consisting of molybdenum, tungsten, magnesium, aluminum or nickel;
and wherein
a is a number from 0.01 to 3;
c is a number from greater then 0 to 0.2;
e and f are numbers from 1 to 9;
x is a number which satisfies the valence requirements of the other elements present;
and wherein at least some of the molybdenum in the catalyst is maintained at a valence state below +6; said catalyst optionally containing one or more elements selected from the group consisting of lithium, silver, cerium, cadmium, cobalt, arsenic, silicon, zinc, germanium, bismuth, ruthenium, platinum and uranium.

2. The catalyst of claim 1 wherein A is tantalum.
3. The catalyst of claim 1 wherein A is zirconium.
4. A catalyst composition of the formula $$A_aD_bE_cTi_dMo_eSb_fO_x$$

wherein
A is at least one element selected from the group consisting of niobium, zirconium, and tantalum;
D is at least one element selected from the group consisting of cadmium, cobalt, arsenic, lithium and cerium;
E is a member selected from the group consisting of molybdenum, tungsten, magnesium, or aluminum;
wherein
a and d are numbers from 0 to 3;
b is a number from 0.01 to 1;
c is a number from 0 to 0.2;
a+d is not zero;
e and f are numbers from 1 to 9;
x is a number which satisfies the valence requirements of the other elements present;
and wherein at least some of the molybdenum in the catalyst is maintained at a valence state below +6.

5. The catalyst of claim 4 wherein D is at least one element selected from the group consisting of arsenic, lithium and cerium.
6. A catalyst composition of the formula $$A_aD_bE_cTi_dMo_eSb_fO_x$$

wherein
A is at least one element selected from the group consisting of niobium, zirconium, and tantalum;
D is at least one element selected from the group consisting of cadmium, cobalt, arsenic, lithium and cerium;
E is a member selected from the group consisting of molybdenum, tungsten, magnesium, or aluminum;
wherein
a is 0.01 to 3;
b is greater than 0 to 1;
c is 0 to 0.2;
d is 0 to 3;
e and f are numbers from 1 to 9;
x is a number which satisfies the valence requirements of the other elements present;
and wherein at least some of the molybdenum in the catalyst is maintained at a valence state below +6.

7. The catalyst of claim 6 wherein b is 0.01 to 0.5.
8. The catalyst of claim 6 wherein E is added to the catalyst as molybdenum metal.
9. The catalyst of claim 8 wherein c is 0.001 to 0.2 and e and f are numbers from 1.0 to 8.0.
10. The catalyst of claim 6 wherein A is zirconium.
11. The catalyst of claim 6 wherein A is niobium.
12. The catalyst of claim 4 wherein a and b are numbers from 0 to 1.2.

* * * * *